United States Patent [19]

Hill

[11] 4,065,714
[45] Dec. 27, 1977

[54] PULSED RF EXCITED SPECTROMETER HAVING IMPROVED PULSE WIDTH CONTROL

[75] Inventor: Howard D. W. Hill, Cupertino, Calif.
[73] Assignee: Varian Associates, Inc., Palo Alto, Calif.
[21] Appl. No.: 698,245
[22] Filed: June 21, 1976
[51] Int. Cl.² ........................................... G01R 33/08
[52] U.S. Cl. ............................... 324/.5 A; 324/.5 R
[58] Field of Search ............... 324/.5 R, .5 A, .5 AC

[56] References Cited

U.S. PATENT DOCUMENTS

| 3,681,680 | 8/1972 | Ernst | 324/.5A |
| 3,781,650 | 12/1973 | Keller | 324/.5 A |

*Primary Examiner*—M. Tokar
*Attorney, Agent, or Firm*—Stanley Z. Cole; Gerald M. Fisher

[57] ABSTRACT

RF excitation for a spectrometer is obtained by pulse width modulating an RF carrier to produce the desired broadband RF exciting spectrum. The RF excitation includes a train of composite RF pulses, each composite pulse having a primary pulse portion of a first RF phase and a second pulse portion of a second RF phase opposite that of the first. In this manner, the finite rise and fall times of the primary pulse portion are compensated for by the corresponding rise and fall times of the secondary pulse portion. The primary pulse portion is lengthened by an amount equal to the secondary pulse portion so that the secondary pulse portion cancels the added primary pulse portion. In a spectrometer the compensating second pulse component removes certain undesired side bands of the RF excitation caused by the finite rise and fall times of the applied RF pulses. The compensating second pulse component removes certain undesired side bands associated with each of the resonant lines of the excited resonance spectrum, thereby simplifying the resonance spectrum of the sample under analysis, particularly for wide band RF excitation.

13 Claims, 16 Drawing Figures

PULSED RF EXCITED SPECTROMETER HAVING IMPROVED PULSE WIDTH CONTROL

BACKGROUND OF THE PRESENT INVENTION

The present invention relates in general to spectrometers employing RF excitation and, more particularly, to improved method and apparatus for generating the RF excitation by use of pulse width modulation of an RF carrier.

DESCRIPTION OF THE PRIOR ART

Heretofore, broadband RF excitation has been employed for exciting RF resonance of a plurality of spectral lines simultaneously. The simultaneously excited resonant spectral lines are detected to produce a composite resonant signal. The composite resonant signal is sampled at time displaced intervals, in the time domain, converted to digital data, stored in a multichannel storage or memory, and time averaged to improve signal-to-noise ratio. The time averaged data is read out of the storage, Fourier transformed from the time domain into the frequency domain to reconstitute a resonance spectrum of the sample under analysis. The reconstituted resonant spectrum is then displayed. Such a radio frequency spectrometer is disclosed and claimed in U.S. Pat. No. 3,475,680 issued Oct. 28, 1969.

It is also known in such broadband RF spectrometers to obtain the broadband RF excitation by pulse width modulating an RF carrier in accordance with a time domain modulation signal synthesized from a table of data stored in a computer. The time domain pulse width modulation signal, derived from the computer, is obtained by selecting a desired RF excitation spectrum in the frequency domain, entering such spectral data into a table in the memory of the computer, Fourier transforming the tabled desired excitation spectrum into the time domain to derive a corresponding table to time domain data, and reading out the tabled time domain data for pulse width modulating the RF carrier applied to the sample for exciting resonance thereof. Such a spectrometer is disclosed and claimed in copending U.S. application Ser. No. 494,802, filed 5 Aug. 1974, which in turn is a continuation-in-part application of copending parent application Ser. No. 350,457, filed 12 April, 1973, now abandoned in favor of the continuation-in-part application and assigned to the same assignee as the present invention.

One of the problems associated with the prior art RF spectrometer employing synthesized broadband RF excitation generated by means of pulse width modulation is that for relatively short pulses, i.e., on the order to 65ns to 65µs in length, such pulses being incremented in increments of 65ns, the finite rise and fall times, on the order of 1µs, introduced certain undesired nonlinearities in the applied excitation resulting in production of certain undesired sideband resonance lines associated with each resonance line of the spectrum. These undesired sidebands of the individual resonance lines cannot be removed by time averaging and unnecessarily complicate the resultant spectral data. Accordingly, it is desired to provide a method of pulse width modulation of the RF carrier which avoids production of the undesired sidebands associated with individual resonance lines.

SUMMARY OF THE PRESENT INVENTION

The principal object of the present invention is the provision of an improved method and apparatus for providing RF excitation for an RF spectrometer of the type in which the applied RF energy is pulse width modulated to produce the desired excitation spectrum.

In one feature of the present invention, the RF excitation is pulse width modulated to produce a train of composite RF pulses. Individual composite pulses include a primary component, of a first radio frequency phase and a compensating secondary pulse component of an opposite phase, whereby finite rise and fall times of the primary pulse component are compensated to prevent excitation of undesired side bands associated with individual resonance lines of the source under analysis.

In another feature of the present invention, the primary pulse component is lengthened by an amount equal to the length of the secondary component so that the resonance effect of the secondary pulse component is cancelled by the lengthened portion of the primary pulse component.

In another feature of the present invention, the pulse width modulation signal, in the time domain, is derived from a table of data stored in the memory of a computer.

In another feature of the present invention, the compensating pulse components are derived by a circuit responsive to a pulse width modulation signal, such compensating secondary pulse component and the corresponding lengthening primary pulse component being added to the input modulation signal by the compensating circuit to derive the composite pulse width modulation signal for modulating the carrier applied to the sample under analysis.

Other features and advantages of the present invention will become apparent upon a perusal of the following specification taken in connection with the accompanying drawings wherein:

DESCRIPTION OF THE PREFERRED EMBODIMENTS

Figure 1:
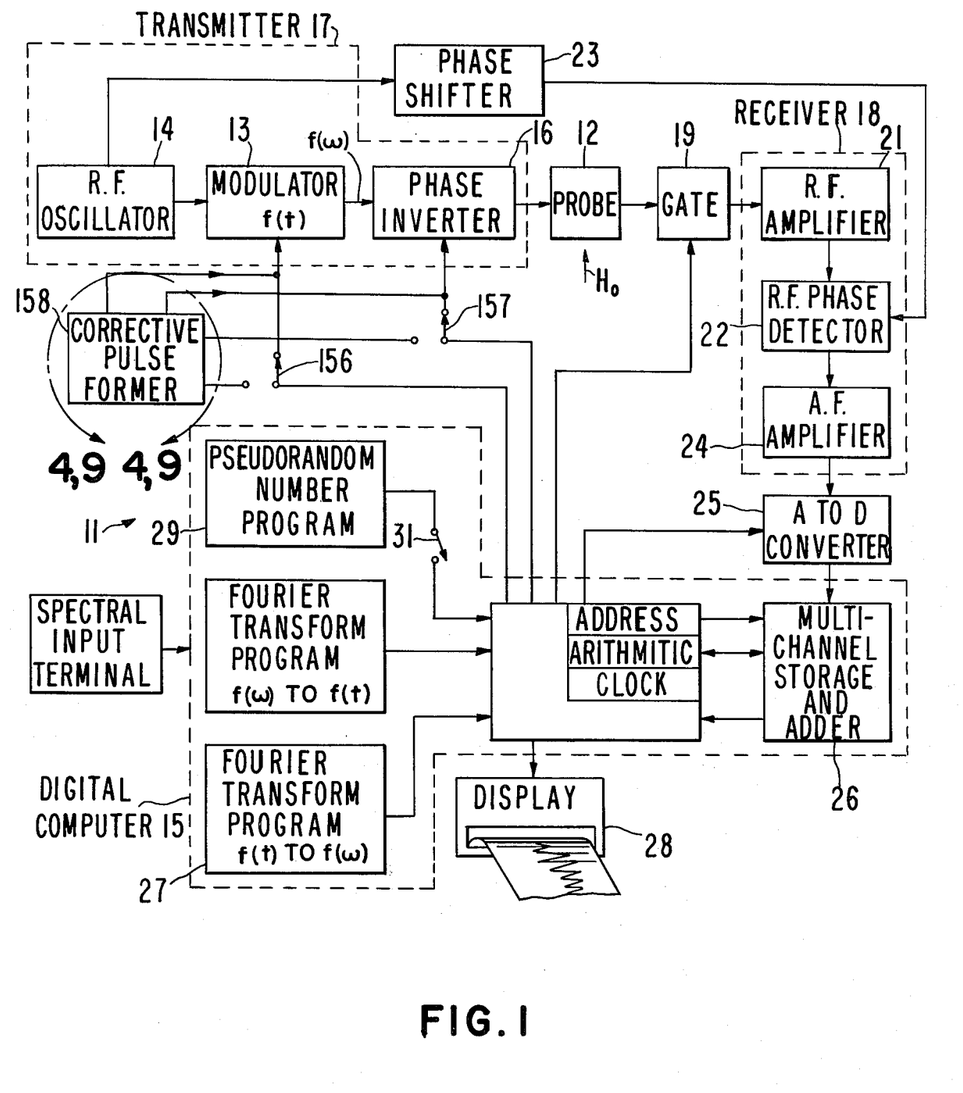
FIG. 1 is a schematic block diagram of a gyromagnetic resonance spectrometer incorporating features of the present invention, FIG. 2 (a-g) is a functional diagram of the spectrometer of FIG. 1 depicting the associated waveforms present in various portions of the spectrometer.

Referring now to FIG. 1, there is shown a Fourier transform gyromagnetic resonance spectrometer 11 incorporting features of the present invention. The spectrometer 11 includes a probe 12 for containing a sample of matter to be analyzed and for immersing the sample in a homogeneous polarizing magnetic field $H_o$. The probe 12 contains a conventional tuned transmitter and receiver RF coil structure for applying an RF magnetic field to the sample with the RF magnetic field vector being applied with a substantial component thereof at right angles to the direction of the polarizing magnetic field vector $H_o$ for exciting gyromagnetic resonance of the sample under analysis.

The RF energy for exciting the coil structure and for exciting resonance of the sample is derived by modulating, in modulator 13, an RF carrier signal supplied from RF osicator 14 with a time varying pulse width modulation function $f(t)$ derived from a computer 15, such as a model 620 $f$ digital computer commercially availble from Varian Associates Inc. of Palo Alto, Calif. Pulse width modulation of the RF carrier produces sidebands on the carrier. The modulation function $f(t)$ is chosen such that the sideband energy has the desired power spectral density for exciting resonance of a plurality of spectral lines of the sample simultaneously. Although the desired power spectral density can vary greatly depending upon the sample to be investigated and the particular desired mode of operation of the spectrometer, a typical example of one type of power spectrum $1F(v)1$ for the resonance exciting RF energy is as shown by spectral waveform (a) of FIG. 2.

Figure 2:
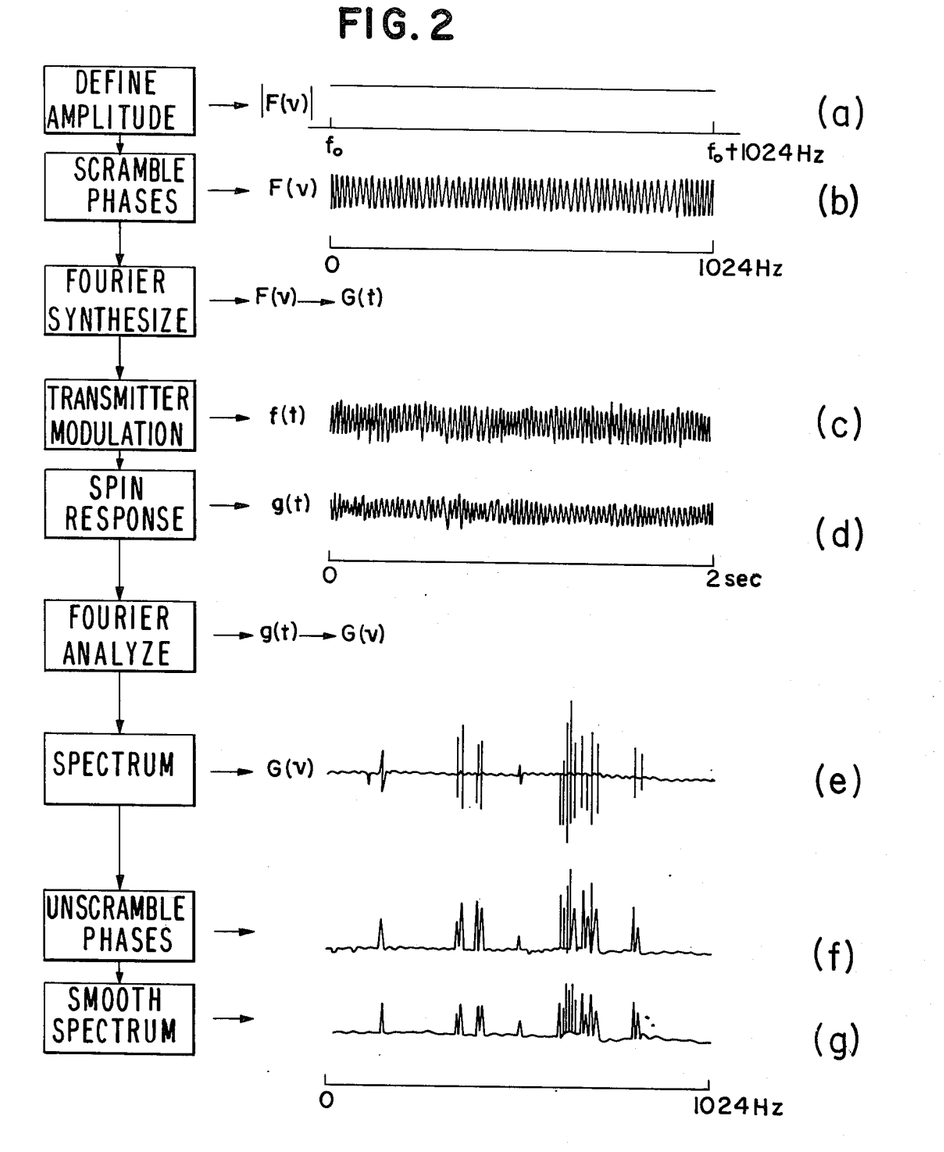

More particularly, in waveform 2(a) the desired RF exciting spectrum is of uniform spectral density over a relatively wide bandwidth, as of 1000 Hz, on both sides of a carrier frequency fo, as of 60 to 100m Hz.

Spectral data is fed into the computer in the form of a Table which tells the computer the amplitude of the real and imaginary components of each frequency of a desired and chosen excitation frequency spectrum $|F(v)|$. For example, the computer 15 is provided with the desired resonance exciting spectrum in the frequency domain, i.e., waveform 2(a), by setting up a Table I, as shown below, consisting of 2N points where N is the number of discrete frequencies in the exciting spectrum. The data may be entered into a spectral input terminal 8 or edited in Table I by being read from a digital input terminal such as a card reader, a Teletype, or a typewriter, or from an analog input device such as devices employing a cathode ray tube light pen combination, a tablet, or joystick; examples of such devices are commercially available from IMLAC Corporation of Waltham, Mass., or the data in Table I may be computed or edited automatically from the data already stored in the computer.

Assuming N is 1024, Table I will contain 2048 rows, two for each frequency component of the 1024 bandwidth (except for $k=O$ and $k=N$) representing two orthogonal components of the vector for each frequency component. One row of each pair is for a digital value corresponding to $[A_k \cos f_k]$ and the other is for a digital value corresponding to $[A_k \sin f_k]$ where $A_k$ represents the amplitude of the frequency component and $f_k$ its phase value at $t=O$. For the spectrum of 2(a), all the values for $A_k$ are equal.

| | TABLE I | TABLE III |
|---|---|---|
| N | AMPLITUDE OF COS/SIN(f) | AMPLITUDE OF COS/SIN(f) |
| 0 | $A_0 \cos (f_0)$ | $A_0 \cos (F_0)$ |
| 1 | $A_{1024} \cos (f_{N_{1024}})$ | $A_{1024} \cos (f_{1024})$ |
| 2 | $A_1 \cos (f_1)$ | $A_1 \cos (f_1+\phi_1)$ |
| 3 | $A_1 \sin (f_1)$ | $A_1 \sin (f_1+\phi_1)$ |
| 4 | $A_2 \cos (f_2)$ | $A_2 \cos (f_2+\phi_2)$ |
| 5 | $A_2 \sin (f_2)$ | $A_2 \sin (f_2+\phi_2)$ |
| 6 | . | . |
| . | . | . |
| 2046 | $A_{1023} \cos (f_{1023})$ | $A_{1023} \cos (f_{1023}+\phi_{1023})$ |
| 2047 | $A_{1023} \sin (f_{1023})$ | $A_{1023} \sin (f_{1023}+\phi_{1023})$ |

For coherent phase, wideband excitation, all values $f_k$ are selected to be equal and the tabled data from Table I is Fourier transformed by the computer to the time domain by means of a conventional discrete Fourier transform program using, for example, the algoithms appearing in Communications of the Association for Computing Machinery, Vo. 11, No. 10, of October, 1968, pages 703 and following, see in particular equations 1–7. This Fourier transformation results in obtaining N pairs of outputs, such transformation values $G(t)$ being tabled in the computer, such as Table II below, where $G(t)_n$ represents the amplitude of the excitation function in the time domain at the time $t_n$.

TABLE II

| TIME | G(t) | $(\Delta t = t_n - t_{n-1} = \frac{1}{2\nu_N})$ |
|---|---|---|
| $t_0$ | $G_0$ | |
| $t_1$ | $G_1$ | |
| $t_2$ | $G_2$ | |
| . | . | |
| $t_n = t_o + n \Delta t$ | $G_n$ | |

The values of $G(t)$ are read out of Table II with the time spacing as indicated in the time column to derive a modulation output function $f(t)$ in the time domain which when employed to modulate the carrier signal in modulator 13 results in producing the desiired sideband power density spectrum as previously programmed into Table I. A typical modulation output function $f(t)$ to produce the power density spectrum of FIG. 2(a) is shown by the waveform of FIG. 2(c), and is essentially a pulse train of RF pulses of short duration at relatively long time spacing.

In a preferred mode of operation, the modulator 13 pulse width modulates the carrier signal with a train of pulses with a repetition rate of 1/500 μs (pulse spacing of 500 μs) and a pulse width of less than approximtely 1/10 the pulse spacing or less than about 50μs. The pulse width is modulated in accordance with the modulation output G(t) of Table II.

Since the value of G(t) from Table II can have both positive and negative sign, a gated phase inverter 16 is provided at the output of modulator 13 for changing the sign, reversing (the phase of the modulated carrier energy fed to the probe 12) in accordance with the sign of the modulation component G(t) read out of Table II.

Cross coupling of RF energy from the the transmitter 17 to a receiver portion 18 of the spectrometer 11, other than through the desired resonance of the sample, is avoided by providing a gate 19 between the probe 12 and an RF amplifier 21 employed to amplify RF resonance signals picked up by the conventional receiver coil in the probe 12. The gate 19 is synchronized by the computer 15 with the timing of the transmitter pulses to provide time sharing.

The output of the RF amplifier is fed to one input of an RF phase detector 22 for phasedetection against a reference phase signal derived via phase shifter 23 from the RF oscillator 14. The output of the phase detector is an audio frequency composite resonance signal consisting of the simultaneously excited resonance spectral line signals emanating from the sample under analysis. The composite audio frequency resonance signal is amplified in audio amplifier 24 and thence fed to an analog-to-digital converter 25 which samples the composite resonance signal once for each transmitter pulse near the end of the period during which the receiver is gated on. The composite resonance signal is sampled near the end of the receiver on time in order that undesirred transient signals associated with the receiver being gated on and off have died out. In an alternate embodiment, not shown, the modulator 13 may also be responsive to the modulation output G(t) to modulate the phase of the RF excitation.

The digitized samples from the output of the A to D converter 25 are stored in succesive channels of a multichannel stoarage and adder portion 26 memory of the computer 15 for time averaging the composite resonance signal. The sampling sequence is synchronized with the readout times $t_o$-$t_n$ of the modulation output of the computer 15 as used to generate the wideband RF excitation $|F(\nu)|$. The sampling sequence repeats with each repeat of the modulation output sequence $f(t)$.

The time-averaged resonance data is then read out of the storage 26 and Fourier transformed via the computer 15 as programmed by a conventional fourier transform program 27 for transforming data in the time domain $f(t)$ into the frequency domain $f(\mu)$ to obtain a resonance spectrum of the sample under analysis. The time averaged resonance spectrum of the sample is then fed to a display for display to the operator and/or for recording. Pure absorption mode, pure dispersion mode, or combinations of absorption and dispersion mode resonance spectral data can be obtained after correction for instrumental effects by reading out the cosine terms of the Fourier transformed data, sine terms of the Fourier transformed data or by reading out combinations of cosine and sine data. The Fourier transformed data is tabled by the computer in a table similar to that of Table I.

One disadvantage to the use of coherent phase wideband RF excitation, as exemplified by waveform of FIG. 2(a), as generated by a pulse train of narrow pulses of carrier energy is that it requires a relatively high intensity RF pulse although the RF excitation is of relatively low average spectral power density. This also introduces a dynamic range problem in view of limited storage and modulator precision. Accordingly, in a preferred embodiment, the phases of the desired RF wideband excitation are scrambled in accordance with a pseudorandom sequence. This is achieved by adding a phase shift value pseudorandomly selected between 0 and $2\pi$ onto each of the cosine and sine values of Table I. In a preferred embodiment the pseudorandom number sequence is provided by a suitable pseudorandom number sequence program 29 which is fed into the computer 15 via switch 31. Such a suitable pseudorandom number sequence program is to be found in an article published in Mathematics of Computations, Vol. 19, page 201, 1965 and in and same journal, Vol. 16, page 368, 1962. The program 29 takes the desired frequency domain spectrum table similar to that of Table I and performs the pseudorandom phase addition to generate a modified table as shown in Table III adjacent Table I above. This is accomplished by taking the values of $\cos f_k$ and $\sin f_k$ components for a given Fourier frequency component and performing the vector multiplication as follows $A_k.\exp(if_k).\exp(i\phi_k)$, where $\phi_k$ is the pseudorandom phase shift value of phase angle. The resultant cosine and sine terms are tabled in Table III. The sequence of values tables in Table III is then Fourier transformed to Table II and read out as previously described to generate the modulation output function $f(t)$ employed for generating the sideband RF excitation. The waveform of FIG. 2(c) shows a typical modulation output for providing incoherent sideband RF excitation.

FIG. 2 shows the functional block diagram for the spectrometer system 11 of FIG. 1 employing phase scrambled RF excitation. The time-averaged and Fourier transformed spectral data will be tabled by the computer 15 in a table similar to that of Table III at $G(\nu)$. This data is unscrambled in phase by subtracting the pseudorandom sequence of phase angles previously added to the data of Table III. The result is a Table of time-averaged resonance spectral data similar to that of Table I which is read out as previously described to obtain pure absorption and dispersion mode resonance spectral data. If only a power spectrum of the sample is desired the Fourier transformed data need not be unscrambled as to phase and may be read out and displayed.

Figure 7A:
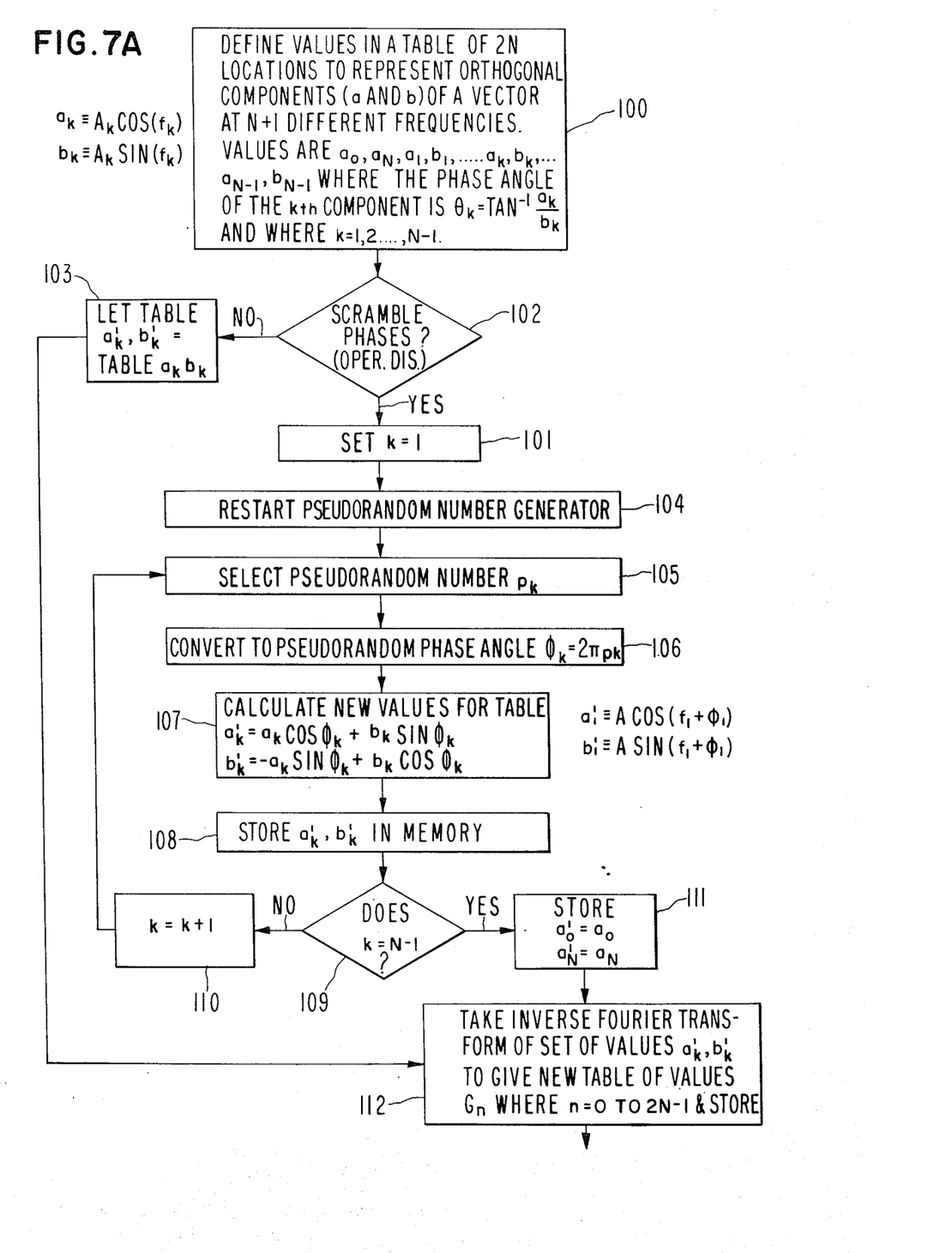
FIG. 7a and FIG. 7b are flow charts of the synthesizing and excitation steps of the present invention.
Figure 7B:
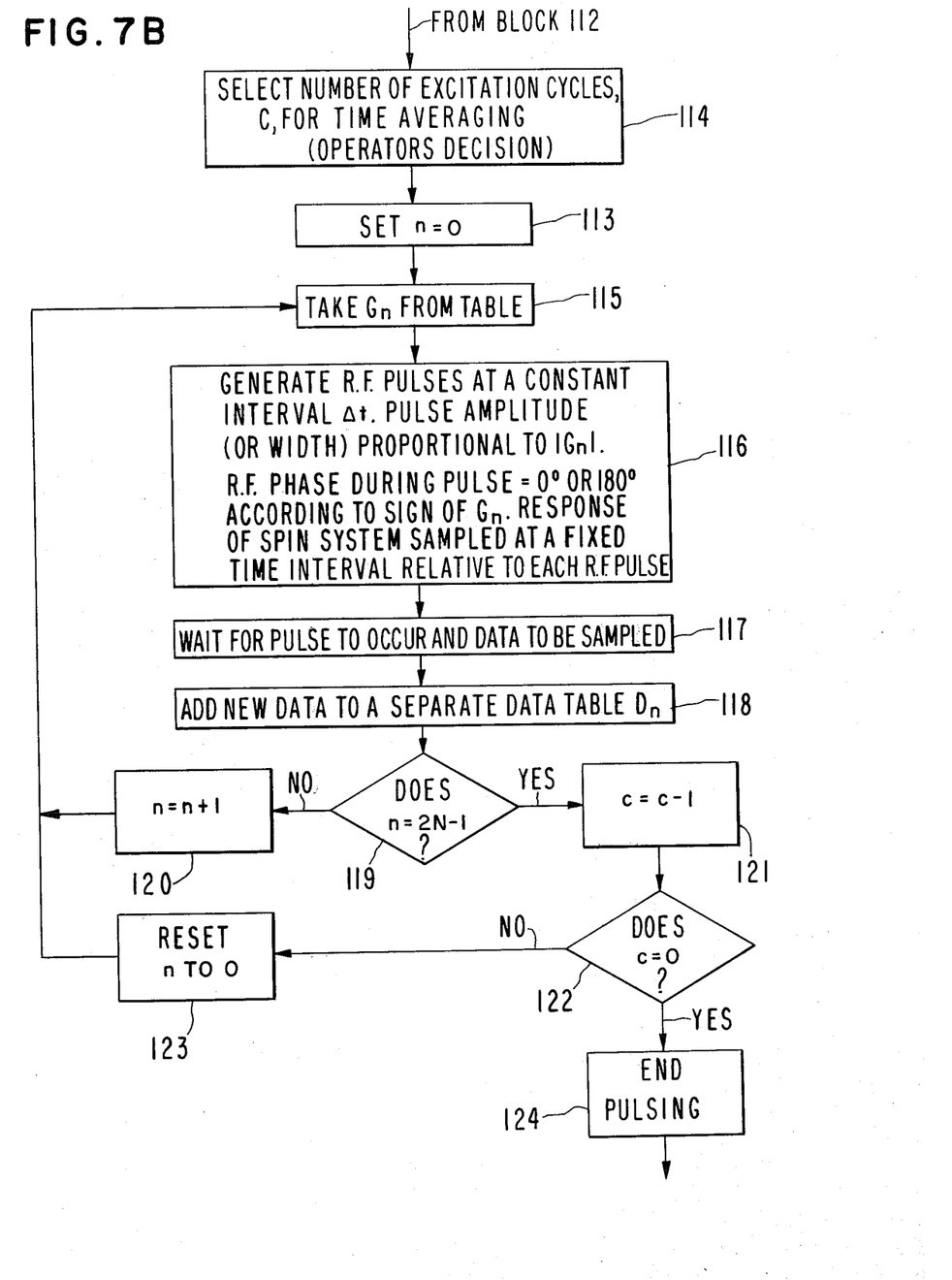

FIGS. 7A and 7B are the flow diagrams of an embodiment of the invention describing steps taken by the computer in converting the operator selected frequency domain excitation spectrum into the desired time domain modulation, for controlling the modulation of RF excitation pulses in width, and for sampling and storing the response of the sample spin system. The data table in block 100 is determined by the operator as described hereinbefore in referennce to Table I and is entered into memory in any convenient manner. Two orthogonal values $a_k$, $b_k$ are defined for each of N=1 frequencies except $a_o$ and $a_n$ which are defined at zero phase angle, hence $b_o=0$ and $b_n=0$.

Assuming the operator has determined in block 102 to scramble phases for power handling considerations, each orthogonal vector $a_k$, $b_k$ is rotated by a pseudorandomly determined phase angle $\phi_k$ and stored in a new table 107 as $a'_k$, $b'_k$. The scramble decision initiates block 101 selecting $a_1$, $b_1$ from block 100 table and causing a pseudorandum generator 104 to start, and to select a pseudorandum number $p_k$ (where $0 \leq p_k \leq 1$), block 105, which is converted to a phase angle, block 106. In block 107 the vector $a_1 b_1$ is rotated by angle $\phi_1$ and the resultant $a_1'$, $b_1'$ is stored in memory block 108. Next, the running index k is interrogated, block 109, and if it is shown to equal less than N-1, the next value $a_k$, $b_k$ is taken from the Table 100 by incrementing $k=k+1$, block 110, and repeating the cycle for each $k+1, 2 \ldots$ N−1. When $k=N-1$, block 109, the storage of $a_o'=a_o$ and $a_N'=a_N$ takes place, block 111, and the inverse Fourier transform of the function represented by $a'_k$, $b'_k$ is taken and stored, block 112.

At this point, the data is now available for modulating the RF excitation appropriately. The decision as to the number of cycles C, block 114, is noted and the modulation process is commenced, block 113, by selecting the value $G_o$ from Table $G_n$, block 115, generating the RF pulse for $t_o$ responsive to $G_o$ in width, and sampling the response, block 117, and storing the received data, block 118. At the time $n$ is set to zero, block 113, the data table $D_n$, block 118, is set to all zeros. If less than $2N-1$ pulses have been applied, block 119, $n$ is incremented, block 120, and the next value $G_n$ is taken from the table to control the modulation of the next pulse and repeat the steps of blocks 116, 117, 118 and 119 until $n=2N-1$. When the value of $n$ reaches $2N-1$, a check on the number of cycles run equals the amount preselected by the operation, block 114. If $c \neq 0$, the process, blocks 116, 117, 118 and 119 is repeated, block 123 until $C=0$ at which time pulsing is stopped, block 124.

Figure 8:
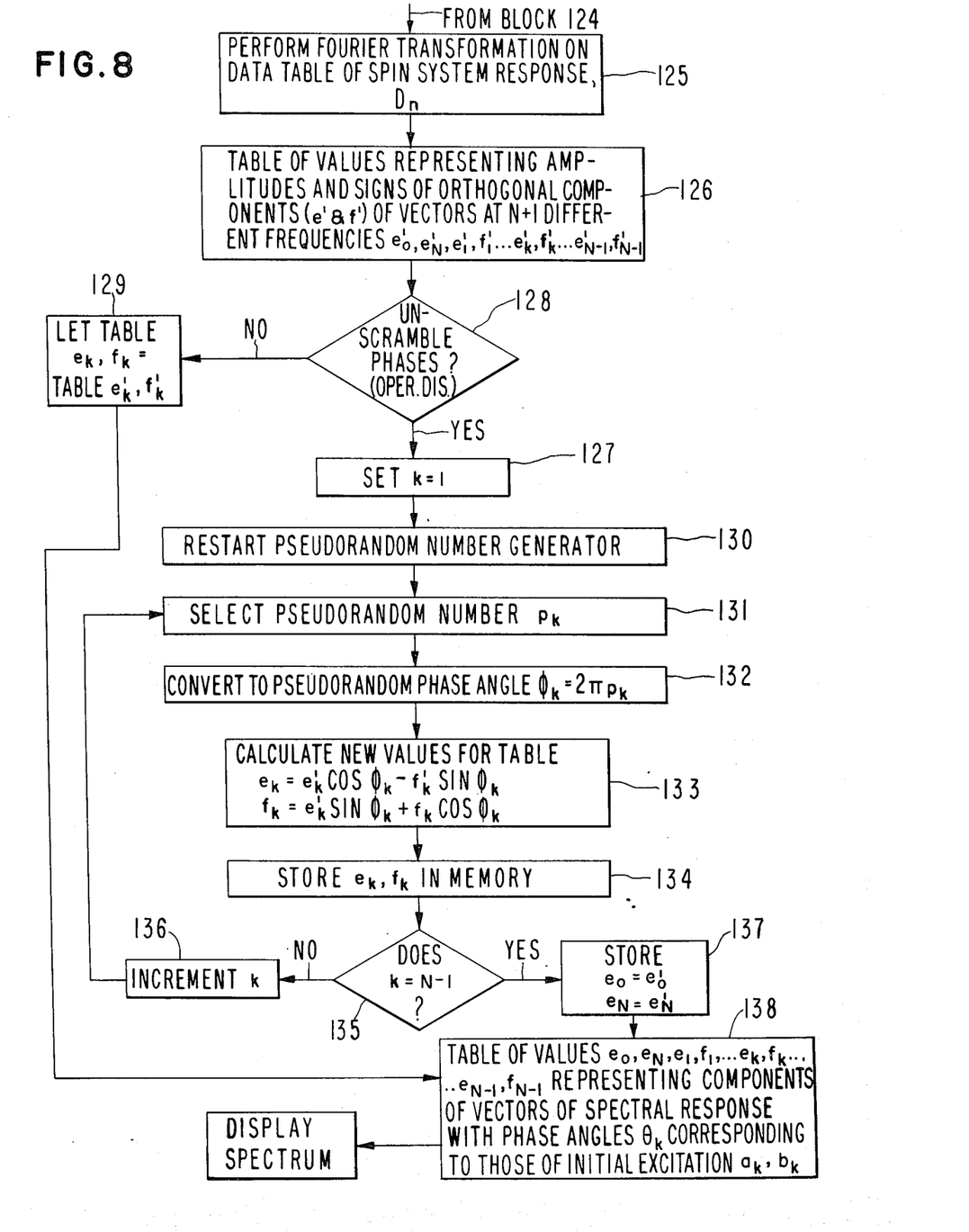
FIG. 8 is a flow chart of a spin system analysis step.

With reference to FIG. 8, the data $D_n$, Table 118, is Fourier transformed, block 125, and the orthogonal values $e'_k$, $f'_k$, of $N+1$ different frequencies are calculated and stored, block 126. If the excitation was not scrambled, block 128, the unscrambling process is commenced by rotating each vector $e'_k$ $f'_k$ through the same pseudorandom angle $\phi_k$ corresponding to that frequency as in block 107, but in the opposite sense, block 133. The unscrambled vectors $e_k$, $f_k$ are stored, block 134, and when all vectors have been counter-rotated, block 135, the $e_o$ and $e_N$ terms are stored, block 137, and the unscrambled spectrum is displayed, block 158.

Figure 3A:
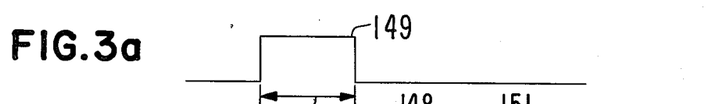
FIG. 3 is a plot showing several of the waveforms in the spectrometer of FIG. 1 and depicting generation of the composite pulse width modulated RF excitation.

As thus far described, the radio frequency carrier signal $f_o$ is pulse width modulated with a series of pulses 149 whose character is shown in FIG. 3a. Each pulse consists of a burst of radio frequency carrier as of 60 to 100 MHz, for exciting nuclear magnetic resonance of the sample, with each pulse having a width varying between 65ns and 65 $\mu$s. The pulse width is incremented in increments, as of 65 ns is length. In such an example, a relatively broad band RF excitation is applied to the sample, such excitation having uniform amplitude over the band of interest.

Figure 3B:
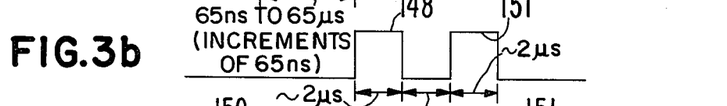
Figure 3C:
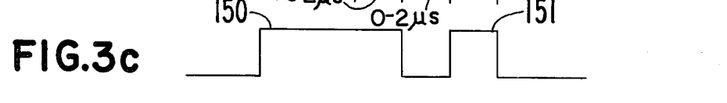
Figures 3D, 3E:
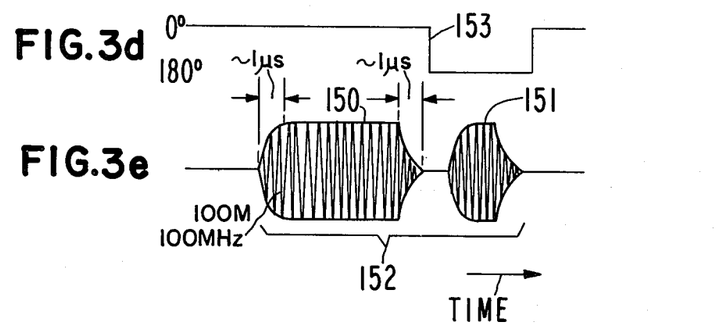
Figure 5:
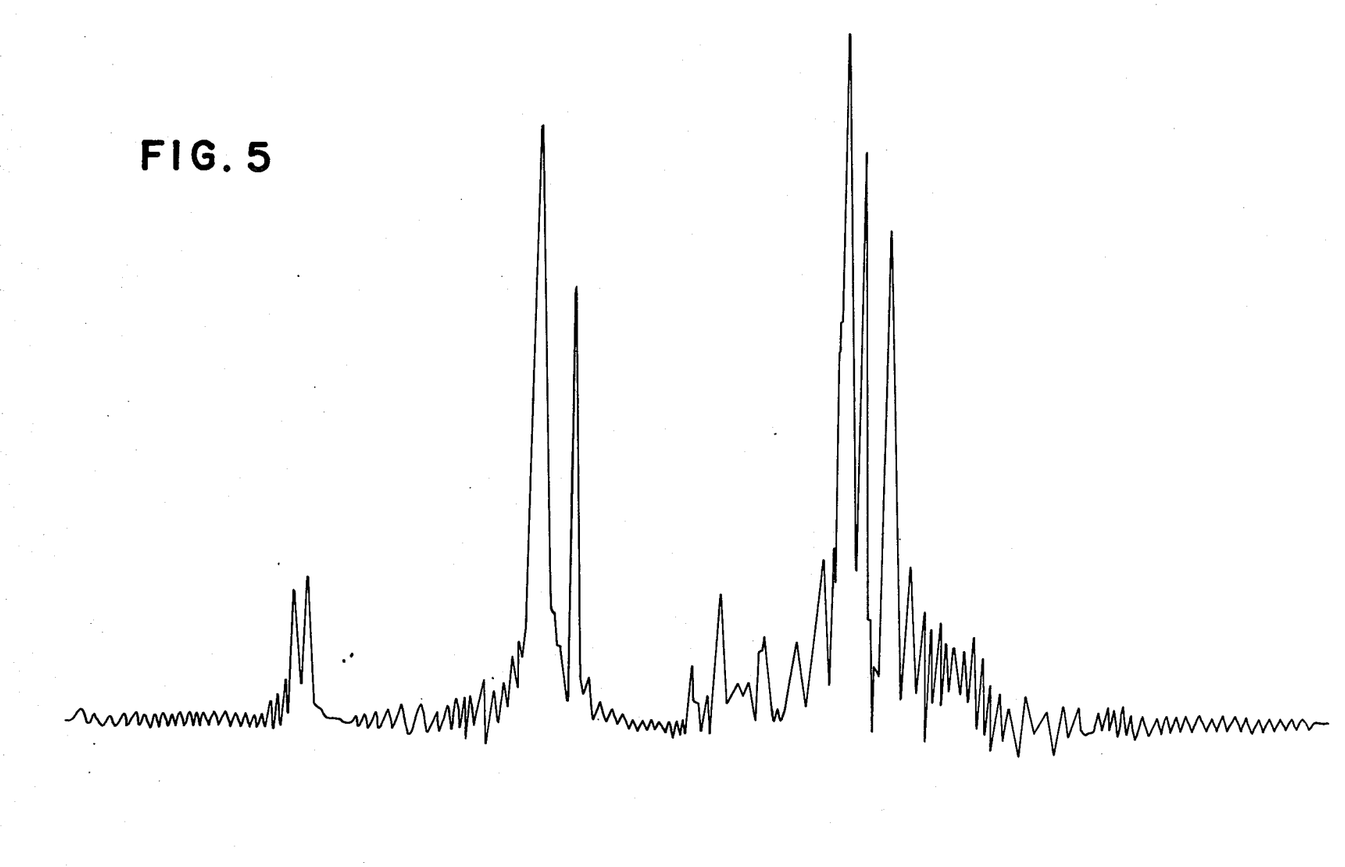
FIG. 5 is a plot of an RF spectrum derived from a sample of matter under analysis showing the prior art undesired side band resonances associated with the various resonance lines.

However, one difficulty is encountered with this prior art pulse width modulation scheme. And that is that the RF energy as fed into the tuned transmitter coil of the probe 12 has a finite rise and fall time as shown in waveform 3d, such rise and fall time being generally on the order of 1 $\mu$s. When operating in the relatively short pulse width regime, as of 65ns, it is seen that the rise and fall time is relatively large compared to the pulse width, and in such a case, the pulse width actually applied to the sample of matter for exciting resonance thereof is not that as determined by the pulse width modulation signal derived from the computer. Therefore, nonlinearities are introduced into the excited resonance producing undesired side bands associated with each of the resonance lines, as shown in the spectrum of FIG. 5.

Thus, according to the present invention, compensating pulse components are added to the basic pulse 149 in such a way as to compensate for the finite and fall time of the pulses of radio frequency energy applied for exciting resonance of the sample. More particularly, a pair of compensating pulse components are added to the basic pulse waveform of FIG. 3a in the manner as shown by waveform 3b. The two pulse components of FIG. 3b are arranged so that the first pulse component 148 has the same phase as that of the desired excitation signal 149 of FIG. 3a as shown in FIG. 3c, thereby lengthening the first pulse component by the amount of the first compensating pulse 148. The phase of the RF energy in the second compensating pulse 151 is opposite to that of the first compensating pulse 148 so that the composite pulse has a primary pulse component 150 of a first RF phase followed by a secondary pulse component 151 of opposite RF phase. In this manner, the resonance exciting effect of the first pulse component 148 as added to the primary pulse 149 is exactly compensated or cancelled by the resonance exciting effect of the secondary pulse portion 151. Moreover, the rise and fall times of the primary pulse 150 are accompanied by equal rise and fall times of opposite phase in the second pulse 151, such that the finite rise and fall times of the primary pulse component are cancelled. In such a case, the combined resonance exciting effect of the composite pulse 152 of FIG. 3c is exactly the same as that of the desired exciting pulse 149 of waveform FIG. 3a, only now the finite rise and fall times are accurately controlled, i.e., the undesired resonance exciting effects derived therefrom are cancelled. The typical composite pulse 152, as shown in waveform 3e, has an RF phase shift control 3d is that applied to the phase inverter 16. The phase shift, as indicated at 153 in waveform 3d is arranged to occur after the fall time of the primary component 150 of the composite pulse 152.

In a typical example, the added compensating pulse components 148 and 151 of waveform 3b each have pulse widths falling in the range of approximately 2$\mu$s with a time between the compensating pulses falling within the range of 0–2$\mu$s.

Also, the compensating pulses 148 and 151 of waveform 3b need not appear at the trailing edge of the resonance exciting component 149 but may just as well appear in advance of the desired resonance exciting pulse 149. Moreover, the delay between the two compensating pulses 148 and 151 of the waveform 3b may go to zero such that the amplitude of the composite pulse need not change between the primary component 150 and the secondary component 151 thereof. All that need be accomplished is a 180° phase shift between the two compensating pulse transmitter coil, a 180° phase shift at a time of excitation of the tuned coil necessarily results in a decrease of amplitude followed by a subsequent increase in the amplitude of the RF excitation in the tuned coil.

Figure 6:
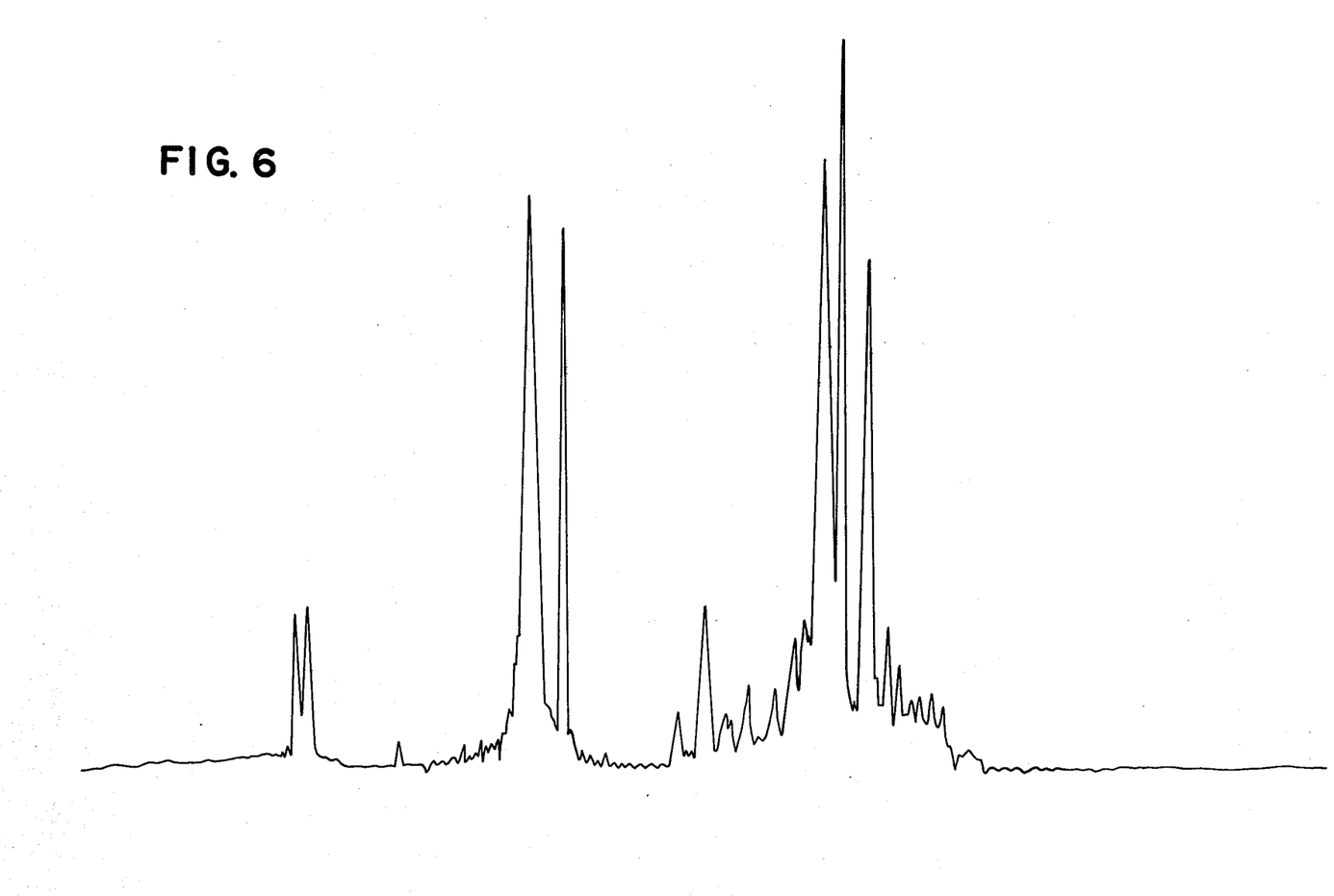
FIG. 6 is a plot similar to that of FIG. 5 obtained using features of the present invention.

A typical resonant spectrum obtained from the same sample used to generate the spectrum and using the compensating composite pulse 152 of FIG. 3e is as shown in FIG. 6. Note that the undesired side bands associated with individual resonance lines of the spectrum have been eliminated, thereby greatly simplifying the resultant resonance spectrum as contracted with the spectrum of FIG. 5.

There are at least two methods by which the compensating pulses of waveform 3b may be added to the desired excitation waveform 3a to derive the composite pulse waveform 3e. In a first method, the time domain function of waveform 3b is merely added to each of the pulse width time domain components of Table II, which is then read out of the table to produce the pulse width modulation signal $f(t)$ in the time domain applied to modulator 13. There is also an associated phase shift component 153 which is fed to the phase inverter 16.

Figure 4A:
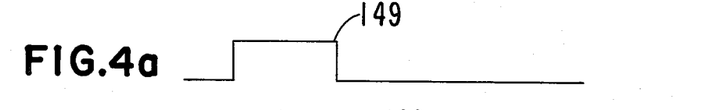
FIG. 4 is a plot of various waveforms associated with the corrective pulse forming portion of the apparatus of FIG. 1 and delineated by line 4—4 thereof.
Figures 4B, 4C, 4D:
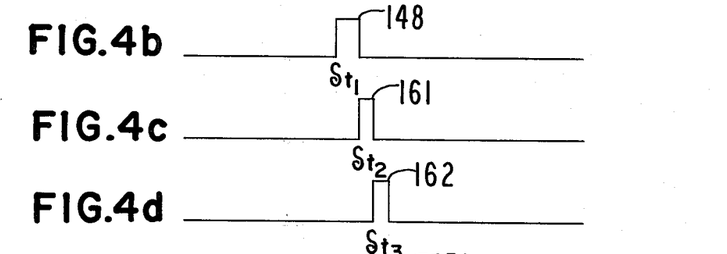
Figures 4E, 4F:
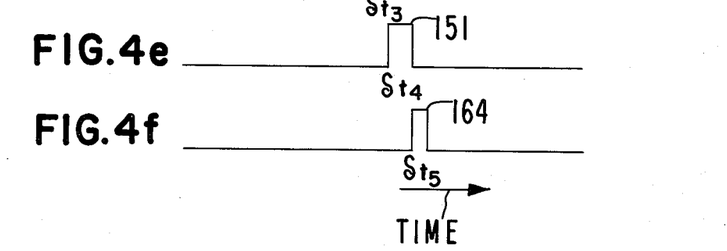
Figure 9:
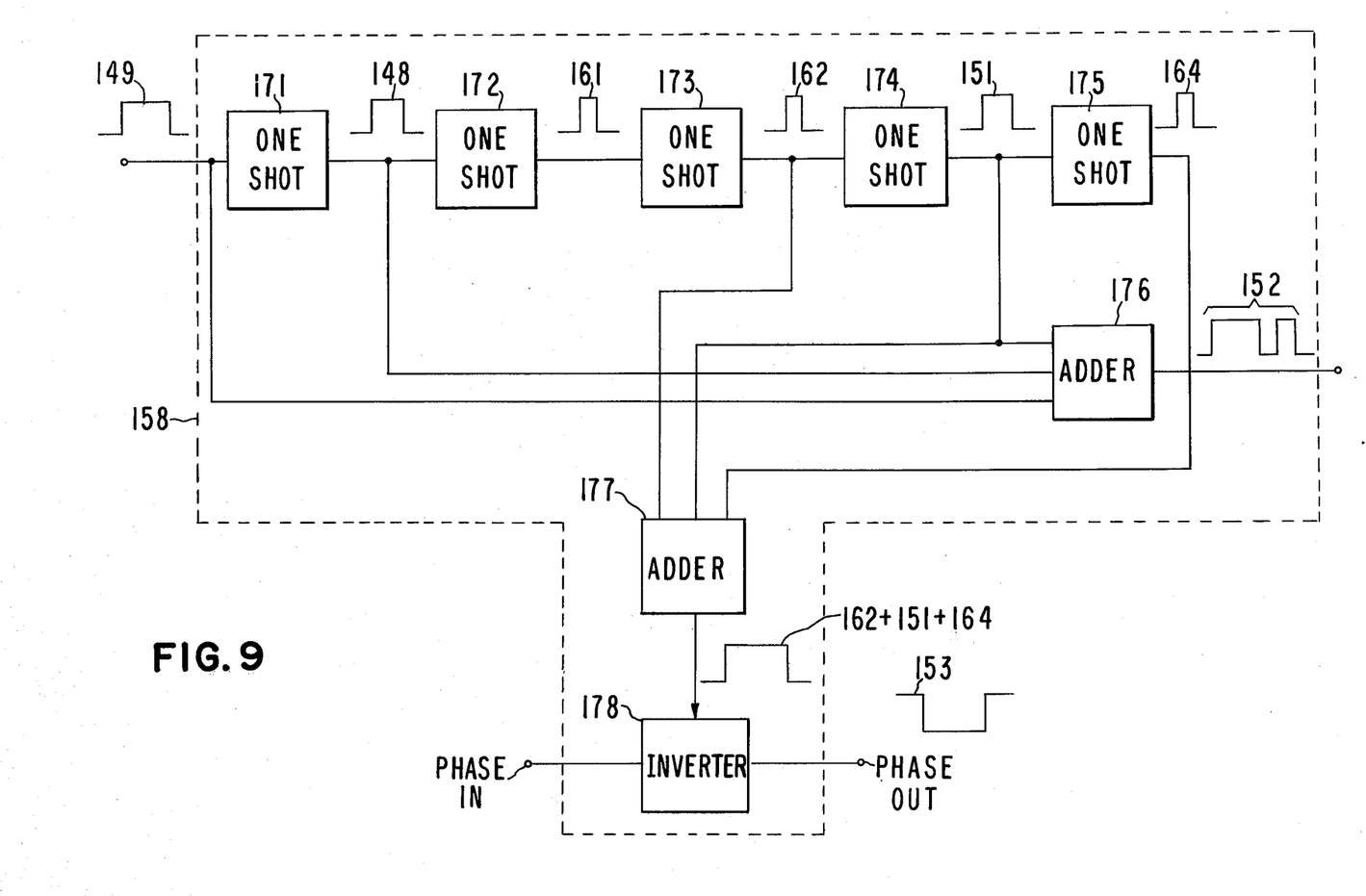
FIG. 9 is a circuit diagram in block diagram form, of that portion of the apparatus of FIG. 1 delineated by line 9—9.

As an alternative to incorporating the compensating pulses of waveform 3b, in the table of data of Table II, the data from Table II may be read out directly and switched via switches 156 and 157 into a corrective pulse former 158 for adding the fixed compensated pulses of waveform 3b to each of the pulses 149. More particularly, as shown in FIGS. 4 and 9, the corrective pulse former circuit 158 generates the composite pulse 152 of waveform 3e by receiving the primary excitation pulse 149 from the output of the computer 15 and also receiving the phase output signal from the computer 15. The computer generated output signal 149 is shown in waveform 4a and is applied via switch 156 to the pulse former circuit 158. The pulse former 158 includes a first one-shot multivibrator circuit 171 responsive to the trailing edge of the input signal 149 for generating a first signal 148, as shown by waveform 4b. Pulse 148 has a fixed predetermined pulse width $\delta t_1$ corresponding in width to each of the compensating pulses 148 and 151 of waveform 3e. A second one-shot multivibrator 172 is responsive to the output pulse 148 of the first multivibrator 171 to generate a second pulse 161 having a pulse width $\delta t_2$ shown in waveform 4c. The pulse widthh $\delta t_2$ of pulse 161 is conveniently one-half of the pulse width $\delta t_1$ of each of the two compensating pulses 148 and 151 of waveform 3b.

Pulse 161 is fed to a third one-shot multivibrator 173 for producing from the trailing edge of pulse 161 a second short pulse 162 of a duration $\delta t_3$ shown in waveforms 4d, such pulse width $\delta t_3$ being conveniently equal to the pulse width $\delta t_2$ of pulse 161. Another one-shot multivibrator 174 is responsive to pulse 162 for generating from the trailing edge thereof the second compensating pulse 151 as shown in waveform 3b and 4e of a pulse width equal to that of pulses 148. The output of the one-shot 174 which produces pulse 151 is fed to another one-shot multivibrator 175 for producing a fifth pulse 164, as shown by waveform 4f. Pulse width $\delta t_5$ of pulse 164 is preferably equal to the pulse widths of pulses 161 and 162. Such pulses have a width preferably longer than the rise and fall time of the RF pulses used to excite the tuned transmitter coil. The output pulses 149, 148 and 151 are added in adder 176 to derive the composite pulse 152. Pulses 162, 151 and 164 are added in adder 177 and the output fed to inverter 178 for inverting the phase of the phase control signal 153 to obtain waveform 3d.

A computer program in assembly language for a Varian Data Machines 620 Computer and corresponding to the computer flow charts off FIGS. 7 and 8 for programming the computer 15 can be found in the patent application file corresponding to this patent as an unpublished addendum.

As used herein, RF spectrometer is defined to include nuclear magnetic resonance spectrometers, electron spin spectrometers, quadrupole resonance spectrometers, microwave absorption spectrometers, RF mass spectrometers, and other types of spectrometers employing RF excitation.

What is claimed is:

1. In a method of exciting and detecting resonance of a sample of matter under investigation in a radio frequency spectrometer, the steps of:
    generating and applying an excitation pulse train of radio frequency energy to the said sample of matter to excite resonance thereof, said pulse train including a train of composite pulses, each composite pulse being shaped to cause the nuclei of said sample to respond as if the composite pulse had substantially zero rise and fall times, each said composite pulse having a primary pulse component of radio frequency energy of a first phase, and an associated secondary pulse component of radio frequency energy of a second phase opposite to that of said first phase, said secondary pulse component being shorter than said primary pulse component, and further, said secondary and primary pulse components having substantially identical rise and fall characteristics whereby the excited nuclei of said sample combine the effects of the first and second phases of said composite pulse excitation so that the detectable nuclei free procession following said composite pulse substantially corresponds to the free precession response of the sample nuclei to a theoretical excitation pulse having a zero rise and fall time.

2. The method of claim 1 including the step of varying the width of each of a plurality of said primary pulse components while retaining a constant pulse width of said associated second pulse components.

3. The method of claim 1 wherein the sample of matter to be excited is excited into gyromagnetic resonance, and the resonance which is detected is the excited gyromagnetic resonance of the sample under investigation.

4. The method of claim 3 wherein the gyromagnetic resonance is nuclear magnetic resonance.

5. The method of claim 1 wherein the step of generating the pulse train of radio frequency energy includes the step of generating radio frequency carrier energy, and pulse width, and phase modulating said carrier with a pulse width and phase modulation signal to produce said pulse train of radio frequency energy.

6. The method of claim 5 including the step of synthesizing said modulation signal from a table of data.

7. In a radio frequency spectrometer for exciting and detecting resonance of a sample of matter under investigation:
    means for generating and applying a train of composite pulses of radio frequency energy to the sample of matter to excite resonance thereof and for causing the nuclei of said sample of matter to respond as if the said composite pulses had substantially zero rise and fall times, each composite pulse including a primary pulse component of radio frequency energy of a first phase and an associated shorter secondary pulse component of radio frequency energy of a second phase opposite to that of said first phase, and
    said means for detecting resonance including means for causing said resonance of said sample of matter to be sampled after excitation of said matter at discrete times following excitation by the complete composite pulse.

8. The apparatus of claim 7 including means for varying the width of each of a plurality of said primary pulse components while retaining a constant pulse width of said associated second pulse components.

9. The apparatus of claim 7 wherein the sample of matter to be excited is excited into gyromagnetic resonance, and the resonance which is detected is the excited gyromagnetic resonance of the sample under investigation.

10. The apparatus of claim 9 wherein the gyromagnetic resonance is nuclear magnetic resonance.

11. The apparatus of claim 7 wherein said means for generating the pulse train of radio frequency energy includes means for generating radio frequency carrier energy, means for pulse width and phase modulating said carrier energy with a pulse width and phase modulation signal to produce said pulse train of radio frequency energy.

12. The apparatus of claim 11 including means for synthesizing said modulation signal from a table of data.

13. In a method of exciting and detecting resonance of a sample of matter under investigation in a radio frequency spectrometer the steps of:

generating an excitation pulse train of radio frequency energy for applying to said sample of matter to excite resonance thereof, said pulse train including a train of composite pulses, each said composite pulse having a primary pulse component of radio frequency energy of a first phase, and an associated secondary pulse component of radio frequency energy of a second phase opposite to that of said first phase, said secondary and primary pulse components having substantially indentical rise and fall characteristics, the difference between the said secondary and primary pulse components being the excitation to which the nuclei respond;

causing the nuclei of said sample to respond as if the excitation pulses had substantially zero rise and fall times by applying said excitation pulse train to said sample; and detecting and recording the resonance response of said nuclei to said excitation pulse train following each complete composite pulse.

* * * * *